United States Patent [19]

Wright et al.

[11] Patent Number: 4,607,551
[45] Date of Patent: Aug. 26, 1986

[54] CENTRIFUGE TUBE-CUTTING APPARATUS AND METHOD

[75] Inventors: Herschel E. Wright, Santa Clara; Robert C. Wedemeyer, San Francisco; Robert H. Giebeler, Jr., Sunnyvale, all of Calif.

[73] Assignee: Beckman Instruments, Inc., Fullerton, Calif.

[21] Appl. No.: 646,280

[22] Filed: Aug. 30, 1984

[51] Int. Cl.⁴ .............................................. B26D 3/16
[52] U.S. Cl. ........................................ 83/54; 83/175; 83/459; 83/520; 269/249; 269/241
[58] Field of Search ..................... 83/14, 19, 54, 175, 83/459, 520; 269/241, 246, 249, 268, 908; 73/863, 863.21, 864.91

[56] References Cited

U.S. PATENT DOCUMENTS

| | | | |
|---|---|---|---|
| 2,880,494 | 4/1959 | Gardner et al. | 269/908 X |
| 3,034,778 | 5/1962 | Shaffer et al. | 269/908 X |
| 3,475,127 | 10/1969 | Gilford | 73/863.21 X |

Primary Examiner—James M. Meister
Attorney, Agent, or Firm—W. H. May; P. R. Harder; L. D. Rish

[57] ABSTRACT

A tube-cutting apparatus and method for separating centrifuged materials are shown in which a resilient axial compressive force is exerted on the tube during cutting by spaced tube-holding members; and the cutting knife has flat upper and lower sides against which the severed portions of the tube are held in sealing engagement by the axial force. Independent adjustment is provided for (a) the relative positions of the tube and the cutting knife, and (b) the relative positions of the spaced tube-holding members.

12 Claims, 25 Drawing Figures

CENTRIFUGE TUBE-CUTTING APPARATUS AND METHOD

BACKGROUND OF THE INVENTION

This invention relates to the centrifuge field, and specifically to the problem of removing separate layers of material from their containers after centrifugation.

Various techniques have been used for separately extracting from a centrifuge tube the materials which have been separated into layers. For example, an aspiration method may be used, in which material from the upper end of the tube is withdrawn by a pipette; or a displacement method may be used, in which an immiscible high density liquid is injected through a hole pierced in the bottom of the tube to sequentially "float out" separate layers containing the desired samples.

The aspiration and displacement techniques are often deficient, in that they tend to re-mix the separated layers, and the displacement technique usually requires piercing of the tube wall.

Another separation technique is cutting through the tube, or pinching it off at the desired location(s).

The cutting technique has the inherent problem of leakage, i.e., material in the tube tends to escape along the surface of the cutting blade. Heretofore, the primary solution of the leakage problem has been the use of rubber grommets, or seals, engaging the opposite sides of the blade.

The use of seals riding against the blade has certain deficiencies, e.g., problems in cleaning the seals after cutting, contamination of the sample by its contact with the seals, and damages to the seals by the cutting blade itself.

In Wright and Wedemeyer Application Ser. No. 453,192, filed Dec. 27, 1982, and having the same assignee as the present application, "Pregrooved Centrifuge Tubes" are disclosed, which facilitate tube slicing by providing one or more grooves in the outer circumference of a centrifuge tube to facilitate its partitioning by slicing. In other words, the tube is sliced at one or more of the grooves, making cutting easier, and also using the groove to guide the cutting blade.

The grooved tube technique is somewhat limited in usefulness by the fact that the groove locations must be determined before the centrifugal separation, as grooving the tube after centrifugation, while technically possible, is economically infeasible.

The present invention is intended to solve the problems discussed above.

SUMMARY OF THE INVENTION

The present invention uses an axial compressive force on a centrifuge tube to maintain an effective seal between the tube walls and the cutting blade during slicing of the tube. The axial force is readily adjustable, and is resilient.

Preferably, the axial compressive force is exerted against the top and bottom of the tube. A convenient, and simple, tube-holding structure is used, which not only provides the requisite sealing force, but also permits high visibility of the tube-contained materials. Thus, the location of the slice can be determined with greater accuracy using the present invention.

The tube is supported circumferentially to minimize tube distortion and resist the blade cutting force during the slicing operation by supports located immediately above and below the cutting plane of the blade.

The present invention includes means for readily adjusting the relative positions of the tube and blade to locate the cutting blade engagement at the desired level. This adjustment does not affect the separately adjusted axial tube-holding force.

An additional feature is the capability of enhancing separated layer visibility by illuminating the tube interior, using a light directed along the axis of the tube, preferably from a "cool" light source, e.g., a fiber optic element transmitting light from a sufficiently remote incandescent lamp.

DETAILED DESCRIPTION OF PREFERRED EMBODIMENT

Figure 1:
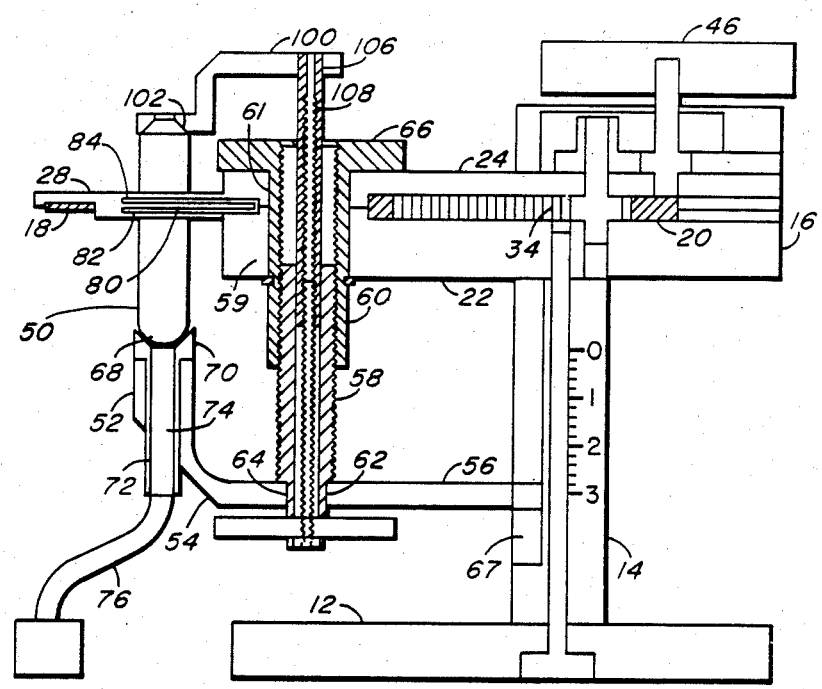
FIG. 1 is a side elevation, partly in cross-section, of the tube holding and tube-cutting apparatus.
Figure 2:
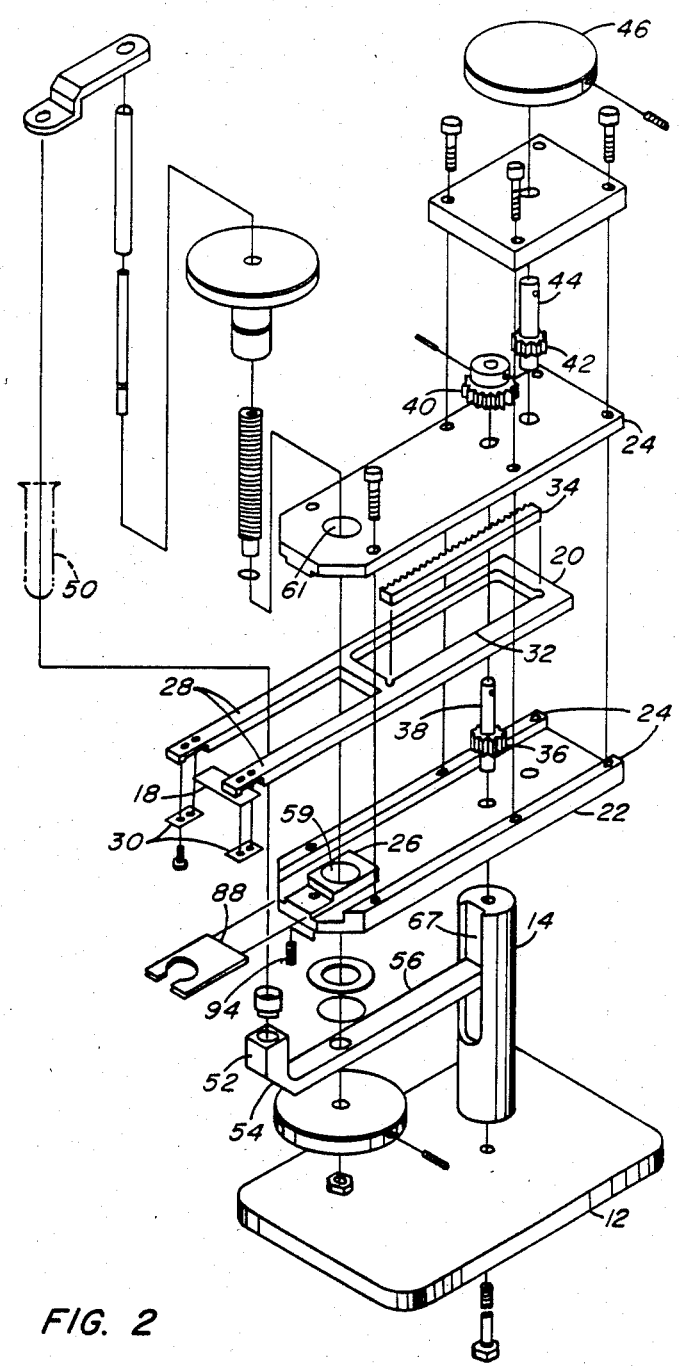
FIG. 2 is an exploded view of the parts of the apparatus in FIG. 1.

FIGS. 1 and 2 show the complete tube-supporting and tube-cutting apparatus. The stationary structure may comprise a platform 12, a vertical post, or column, 14, and a support sub-assembly 16 mounted on the post 14 and providing support for both the tube and the cutting means.

Figure 4:
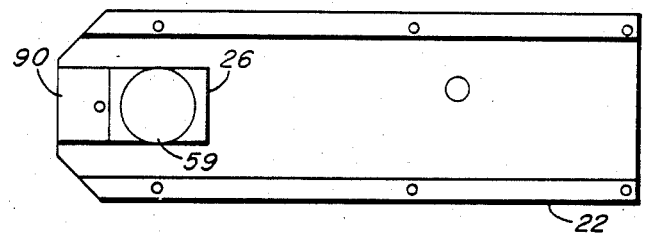
FIGS. 4 and 5 show the lower housing of the support subassembly on which the blade-carrier rests, FIG. 4 showing a plan view, and FIG. 5 a cross-section on line 5—5 of FIG. 4.
Figure 5:
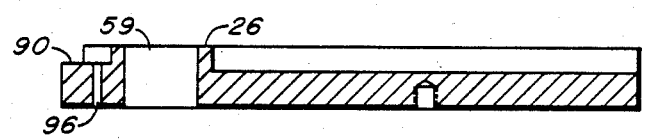
Figure 6:
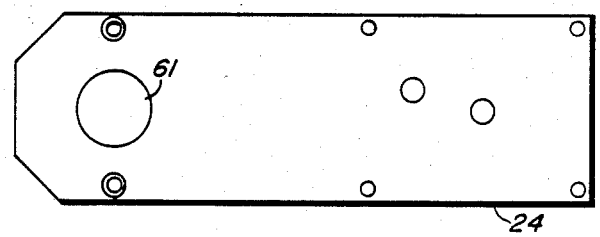
FIGS. 6–8 show the upper housing of the support subassembly, which is secured to the lower housing, FIG. 6 showing a plan view, FIG. 7 a side view, and FIG. 8 an end view.
Figure 7:
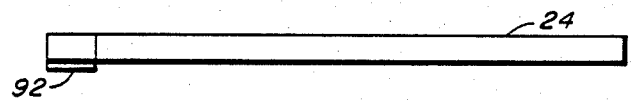
Figure 8:
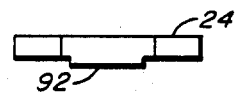

As seen more clearly in FIG. 2, the support subassembly 16 both (a) supports and guides a horizontally-movable cutting blade; and (b) provides a cantilevered support for a vertically-oriented tube. Conveniently, a cutting blade 18 is secured to a bifurcated end of a horizontally slidable blade-carrier 20. The blade carrier 20 is clamped between a lower housing member 22 and an upper housing member 24, which are secured together to constitute the support sub-assembly 16. Lower housing member 22 (seen also in FIGS. 4 and 5) has longitudinally-extending side ridges 24, between which the blade-holder 20 is guided in its reciprocal movements. Additional guidance of blade 18 is provided by an integral rectangular boss 26 formed on member 22, which confines, between its edges and the side ridges 24, the two branches 28 which constitute the bifurcated end of blade-holder 20. The blade 18 is secured to the branches 28 by suitable fastening means 30, with the cutting edge of the blade in the open space between the branches 28, and preferably facing toward post 14.

Means for moving blade 18 toward and away from post 14 may be provided by a rack and pinion drive. Blade-holder 20 has a slot 32 which receives a rack member 34, having teeth which engage a pinion gear 36. Rotation of gear 36 moves the elongated rack 34, which engages the end walls of slot 32 to drive the blade-holder. A shaft 38, to which gear 36 is secured, also is secured to a gear 40, which is driven by a smaller diameter gear 42. Gear 42 is secured to a shaft 44, which may be rotated manually by a control knob 46. The mechanical advantage of the gear train provides adequate tube-cutting force at the blade.

Figure 13:
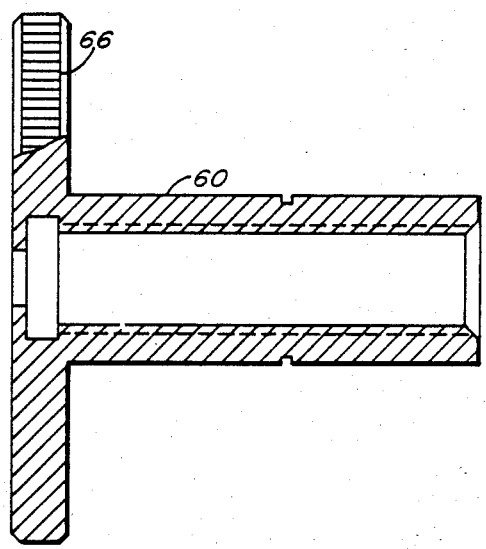
FIGS. 13 and 14 are cross-sectional views showing, respectively, the upper and lower members whose threaded interconnection permits adjustability of the tube with respect to the cutting blade.
Figure 14:
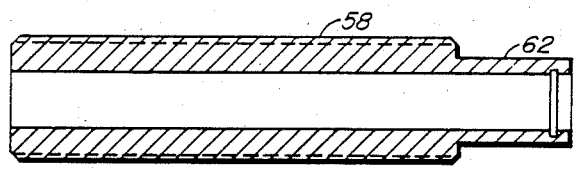

A tube 50, containing layers of material after centrifuging, is shown in its supported position in FIG. 1. Its lower end is carried by a vertical arm 52 of an L-shaped bracket 54, which has a horizontal arm 56 upheld by support sub-assembly 16. The vertical support of bracket 54 is provided by the threaded interconnection of a sleeve 58 (shown in cross-section in FIG. 14) with a sleeve 60 (shown in cross-section in FIG. 13), which extends through openings 59 and 61 in the housing members 22 and 24. As shown, the sleeve 58 is externally threaded, and has its lower end 62 press-fitted in a hole 64 in horizontal arm 56 of bracket 54. The sleeve 60 is internally threaded, and is formed integrally with a knob 66, which rests on top of the upper housing 24 of support sub-assembly 16. The horizontal arm of L-shaped bracket 54 extends into a vertically-extending channel 67 in post 14. The end of arm 56 is guided in channel 67, which prevents movement of the arm in a horizontal plane, but permits vertical movement for adjustment purposes.

The lower hemispherically-formed end of tube 50 may rest on a conical surface 68 provided by a tube-stop member 70, which is supported on vertical arm 52 of bracket 54, and which has a downwardly-extending body portion 72, through which a passage, or post, 74 is formed. The purpose of passage 74 is to permit coaxial illumination to be applied to tube 50 through the bottom of the tube. Preferably, such illumination is applied by a fiber optically transmitted light source 76. The fiber optic transmission has the advantage of low heat, which is important because heat might cause remixing of the layers in the centrifuged contents of the tube.

Because knob 66 is supported on the cantilevered end of support sub-assembly 16, and because members 58 and 60 have threaded inter-engagement, turning knob 66 causes vertical adjustment of the position of tube 50. This adjustment is required to accomplish tube slicing at exactly the level desired for separation of the centrifuged materials. The tube position can be determined either by visual alignment of its contents, or by using a suitable scale. A scale 3 cm long is shown on post 14. By using threads on members 58 and 60 having the required pitch, a 360° rotation of knob 66 can represent the vertical distance between two markings on the vertical scale, which are shown having two mm intervals (one-fifth cm). In other words, one revolution of knob 66 may provide a range of positions from 0 to 2 mm.

Figure 9:
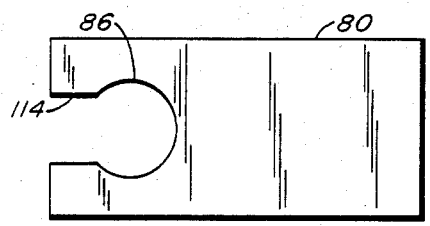
FIGS. 9 and 10 show an element which provides upper and lower metal supports between which the blade is retained as it cuts the tube, and which also provides reaction force on the tube against the horizontal cutting force, FIG. 9 showing a plan view, and FIG. 10 a side view.
Figure 10:
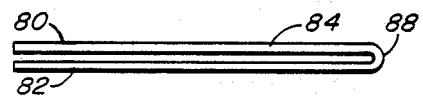

FIGS. 9 and 10 show a dual function element 80 which provides upper and lower flat surfaces between which the blade moves, and which also provides horizontal reaction force on the tube opposed to the cutting force and located as close as possible to the cutting level. The element 80 may conveniently be formed by folding over a sheet metal strip to provide a lower support layer 82 and an upper support layer 84. Aligned holes 86 extend through the lower and upper strips. The tube 50 is inserted through the holes 86, which fit the tube closely enough to give it circumferential support during the cutting process. In other words, the tube's support inside holes 86 provides both: (a) reaction force against the cutting force, and (b) peripheral support to prevent collapsing of the tube. The blade 18 slides between the lower and upper strips 82 and 84, which prevent undesired vertical displacement of the blade during cutting. The ease of manufacturing and replacing element 80 is important, because different blades (and, therefore, different elements 80) are needed for different size tubes.

Referring to FIG. 2, it will be apparent that the folded-over end 88 of element 80 is butted against boss 26 on lower housing member 22, and is laterally confined between the bifurcations 28 on blade-carrier 20. Vertically, element 80 is confined between two slightly raised surfaces, upwardly-facing surface 90 on lower housing member 22, and downwardly-facing surface 92 on upper housing member 24. During the forward, or cutting, stroke of blade 18, which moves toward post 14, the reaction force is provided by engagement of the tube with element 80, which itself exerts a force against boss 26. During retraction of the blade, displacement of element 80 is prevented by a set screw 94 which is inserted through a threaded opening 96 in lower housing member 22, in order to exert an upward clamping force on element 80.

Figure 15:
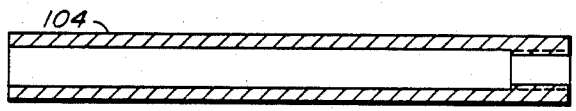
FIGS. 15 and 16 are views showing, respectively, the upper (cross-section) and lower (side-elevation) members whose threaded interengagement permits adjustability (a) to compensate for different tube heights, and (b) to exert the desired axial compressive force on the tube.
Figure 16:
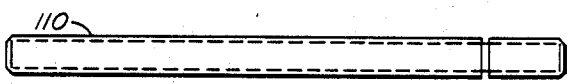

An important feature of the present invention is the retaining force exerted on the tube 50 along its axis. This is a compressive force between the conical surface 68 on member 70 and a clamping arm 100 which has, near its outer end, a downwardly-facing conical surface 102 adapted to engage (and also retain laterally) the top of the tube. Axially-directed compressive force on the tube is created by tightening a threaded connection between an upper member secured to the inner end of arm 100 and a lower member which butts against the bottom of the structure which supports the bottom of the tube. The upper member 104 (shown in FIG. 15) has its upper end press-fitted into a hole 106 in arm 100, and has a downwardly-extending, internally-threaded sleeve 108. The lower member 110 (shown in FIG. 16) is a long screw having its threads in engagement with those of sleeve 108. A knob 112 is secured to screw member 110, so that rotation of the knob tightens or releases the tension between the upper and lower tube-engaging surfaces.

It is desirable to exert a reasonable axial compressive force on tube 50. This, of course, has to be limited by the strength (thickness) of the tube wall. The force on the tube causes the tube sections to seal against the upper and lower surfaces of the blade, as the tube is cut through. This effectively prevents leakage of the centrifuged material from either portion of the tube. The axial compressive force needs to be sufficient to maintain the sealing effect, but not enough to cause undue friction (braking action) between the blade and the tube.

It is also desirable that the force be resilient, in order that the tube will be retained under pressure, and its sections will be re-engaged (and effectively re-sealed) after the blade has passed completely through the tube. The resiliency is provided by the cantilevered arrangement of arm 100, which permits reasonable deflection of the arm as the threaded connection of members 104 and 110 is tightened.

Because the vertical clamping pressure on tube 50 is exerted at its upper and lower ends, visibility of the tube and its contents is maximized. This simplifies the adjustment of the tube position for making a cut at the right location. If additional visibility adjacent the cut location is desired, the outer ends of the upper and lower strips of the tube's horizontal support element 80 may be notched, as shown at 114 in FIG. 9. The notches 114 extend from the ends of the strips to the vertically-aligned openings 86, thereby providing unrestricted visibility of the layered contents of the tube, while still supporting the tube laterally in the required manner.

Figure 11:
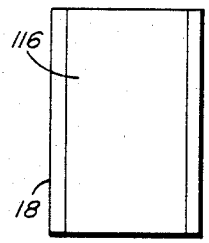
FIGS. 11 and 12 showing the tube-cutting blade, FIG. 11 showing a plan view, and FIG. 12 a side view.
Figure 12:
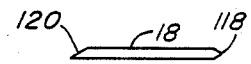

FIGS. 11 and 12 show the preferred shape of the blade 18. As shown in FIG. 11, from the top, the blade has a central flat surface 116 (both top and bottom) which has substantial area (greater than the cross-sectional area of the tube). As seen in FIG. 12, a cutting edge 118 (ground both above and below) is formed along the front of the blade (as it faces the tube), and a chamfered trailing edge 120 is formed along the rear of the blade.

Figure 18A:
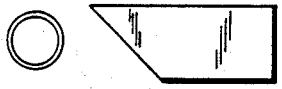
FIGS. 18A–18D show plan views of types of blade cutting edges which might be substituted for the straight blade cutting edge of FIG. 11.
Figure 18B:
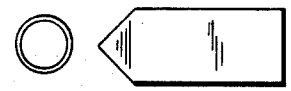
Figure 18C:
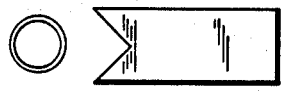
Figure 18D:
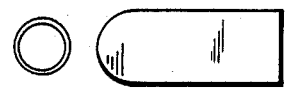

Various shapes of the blade cutting edge may be used, other than the "right-angle engagement" blade of FIGS. 11 and 12. Examples of other cutting edges are shown in FIGS. 18A to 18D. FIG. 18A shows a "guillotine" blade cutting edge; FIG. 18B shows a "dagger" blade cutting edge; FIG. 18C shows a "vee" blade cutting edge; and FIG. 18D shows a curved blade cutting edge.

FIGS. 17A-17E show progressive relative positions of blade 18 and tube 50, as a tube section is being sliced. Although the present disclosure involves movement of the blade while the tube is held stationary, the tube could be moved against a stationary blade, or both blade and tube could be moved. The necessary motion is relative movement of blade and tube along a plane substantially perpendicular to the longitudinal axis of the tube.

Figure 17A:
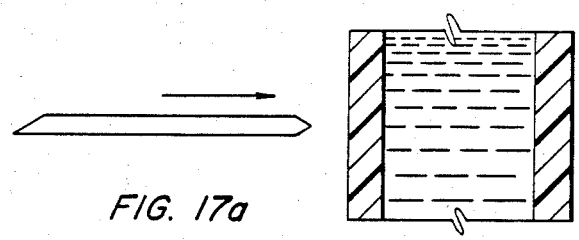
FIGS. 17A–17E show, in closeup, a series of relative positions of the blade and tube as the cutting process proceeds.
Figure 17B:
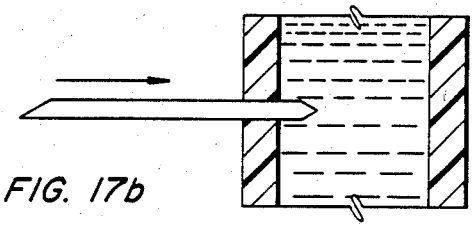

In FIG. 17A, the blade cutting edge 118 is approaching the near side of the tube, as indicated by the arrow. In FIG. 17B, the cutting process has begun; and in FIG. 17C, the blade has cut entirely through the tube. At this point, the blade movement will usually be stopped momentarily. The upper and lower sections of the tube have completely separated. The axial compressive force on the tube causes its walls to seal effectively against the upper and lower flat surfaces of the blade. Direct engagement of the tube wall material (typically a polymer) against the metal surfaces of the blade creates the sealing effect. Later, the blade surfaces can be readily cleaned, avoiding the contamination problems encountered with prior art devices. Also, contamination is avoided because the tube itself provides the seal; and the seal is discarded after each tube sample has been fractionated.

Figure 17C:
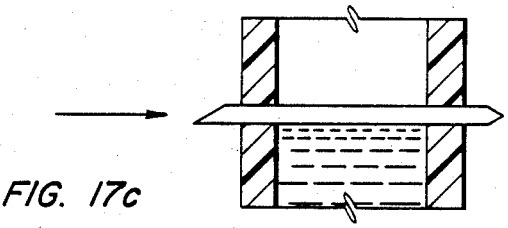

While the blade and tube are in the relative positions shown in FIG. 17C, customarily the material above the blade will be removed by aspiration for suitable analytical procedures. The upper portion of the tube and the top of the blade may then be thoroughly cleaned.

Figure 17D:
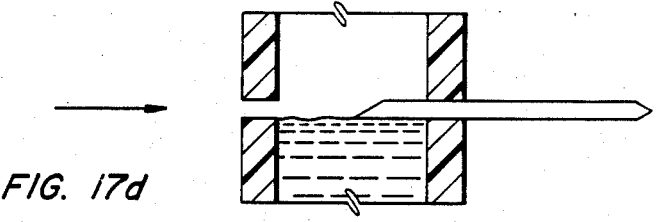
Figure 17E:
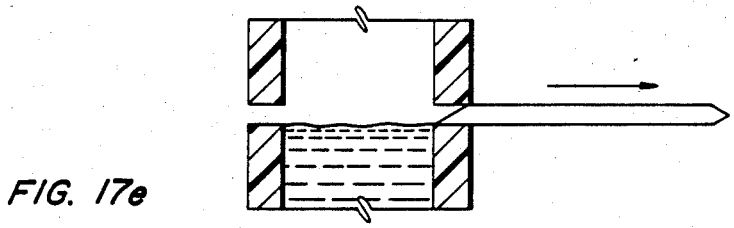

It is not desirable to disengage the blade by retracting it from the sliced tube. This is true because the cutting edge 118, as it retracts over the entering side of the tube, leaves a slight gap, through which meniscus from the lower section of the tube would tend to be drawn by the surface tension attraction between the cutting edge of the blade and the material. In order to avoid this leakage, the blade should be moved on through the tube, as shown in FIGS. 17D and 17E. Also, it is desirable that the trailing edge 120 of the blade (a) be flat along its bottom surface, as shown, and (b) have a sloping upper edge (chamfered, as shown) so that only a thin metal edge will be in engagement with the material in the lower section of the tube as the blade leaves the tube.

As shown in FIGS. 17D and 17E, the axial pressure on the tube will probably not close the gap caused by the slicing action, until the blade has passed completely through the tube. Then the resilient axial force will push the tube sections together, creating a satisfactory seal. This permits the upper tube section to act as a "splash container" while the remaining material in the lower tube section is worked with, using whatever method is appropriate.

It is possible to slice the tube again at a lower position (or positions). In order to retract the blade, it would be desirable to loosen the pressure on the tube, remove the upper tube section, lower the remaining portion of the tube, and retract the blade without engaging the tube. Thereafter, the vertical position of the tube can be adjusted, in order to make another cut lower on the tube. In a somewhat different embodiment, it would not be necessary to retract the blade. The blade would be removed, the blade carrier retracted and the blade reinstalled for the additional cuts. In order to have a really effective seal after the cut tube sections have been rejoined, it is desirable to rejoin them without significant change from the original, at-time-of-cut, location. Once released and removed it might prove quite difficult to relocate the tube parts with the necessary precision.

Figure 3:
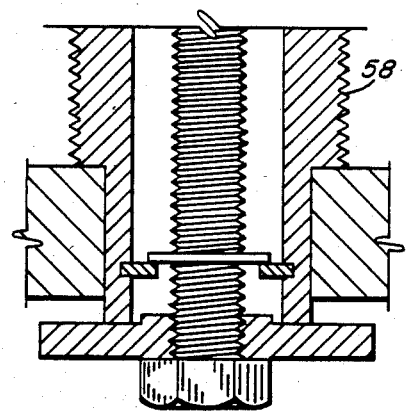
FIG. 3 is an enlarged cross-section of a small segment of FIG. 1.

After the threaded connection between screw 110 and sleeve 104 has been loosened, and the tube has been removed, the subassembly comprising arm 100 and members 104 and 110 would tend to drop down, unless a temporary support has been provided. Such a support is shown in FIG. 3. A snap ring 120 held in an exterior groove 122 on screw 110 is adapted to rest on a snap ring 124 held in an interior groove 126 in sleeve 58.

From the foregoing description, it will be apparent that the apparatus and method disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. An apparatus for separating components after a centrifuge operation, the components being in layers in a generally tube-like container, comprising:
    container-holding means having elements which engage the container at spaced locations and are adapted to provide axially-directed compressive force on the container wall; and a cutting means adapted to cut transversely through the container wall at a desired level, the cutting means having flat upper and lower surfaces large enough to cover the cross-sectional area of the container;

the axially-directed compressive force on the container wall creating a sealing engagement of the severed edges of the container wall against the flat upper and lower surfaces of the cutting means.

2. The apparatus of claim 1 in which the container-engaging elements are in engagement with opposite ends of the container.

3. The apparatus of claim 2 in which at least one of the container-engaging elements provides a resilient force which maintains continuous sealing pressure on the container wall, both during and after cutting of the wall.

4. The apparatus of claim 1 which also comprises:
a supporting structure supporting both the cutting means and the container-holding means; and
means carried by the supporting structure for adjusting the relative locations of the cutting means and the container holding means, thereby permitting adjustment of the level at which the container will be cut.

5. The apparatus of claim 2 which also comprises:
a container-engaging member adjacent the cutting means which exerts transverse resistance on one side of the container against the force of the cutting means on the other side of the container.

6. The apparatus of claim 2 in which at least one container-engaging element has a passage therein, and means for causing axially-directed illumination of the container's contents via the passage.

7. The apparatus of claim 6 in which a fiber optic element provides illumination via the passage.

8. A method of sectioning a tube, which contains layered materials after centrifugation, comprising:
holding the tube between spaced tube-holding members which exert an axial compressive force on the tube;
causing a blade to engage the tube in a direction intersecting the tube axis;
supporting the tube and blade on the same supporting structure;
adjusting the relative positions of the tube and blade to select the desired level of separation of materials; and
causing relative movement of the blade and tube in order to cut through the tube at the selected level;
using the axial compressive force on the tube to seal the separated tube sections to the upper and lower surfaces of the blade.

9. The method of claim 8 which also comprises:
exerting a blade-opposing reaction force on the tube immediately adjacent to the blade.

10. The method of claim 8 in which a connection between the upper and lower tube-holding members is adjusted to compensate for different tube lengths and to vary the axial compressive force on the tube.

11. An apparatus for cutting a centrifuge tube after centrifugation comprising:
a supporting structure;
a first tube-engaging member at the bottom of the tube;
an adjustable connection between the first tube-engaging member and the supporting structure by means of which the tube position relative to the supporting structure may be varied;
a second tube-engaging member at the top of the tube;
an adjustable connection between the first and second tube-engaging members by means of which axially-directed compressive pressure on the tube may be exerted;
a tube-cutting blade supported and guided by the supporting structure for movement in a plane which intersects the longitudinal axis of the tube; and
a laterally-acting tube-supporting element carried by the supporting structure, located adjacent the blade, and engaging the outer wall of the tube opposite the cutting edge of the blade in order to provide support for the tube adjacent the plane of the blade's cutting action.

12. The apparatus of claim 11 in which the laterally-acting tube-supporting element comprises a fold-over metal strip having upper and lower strips extending, respectively, along the upper and lower surfaces of the blade.

* * * * *